United States Patent
Hendriks et al.

(10) Patent No.: US 11,412,985 B2
(45) Date of Patent: Aug. 16, 2022

(54) BIOPSY GUIDANCE BY IMAGE-BASED X-RAY SYSTEM AND PHOTONIC NEEDLE

(71) Applicant: KONINKLIJKE PHILIPS N.V., Eindhoven (NL)

(72) Inventors: Bernardus Hendrikus Wilhelmus Hendriks, Eindhoven (NL); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 755 days.

(21) Appl. No.: 16/388,909

(22) Filed: Apr. 19, 2019

(65) Prior Publication Data
US 2019/0313976 A1 Oct. 17, 2019

Related U.S. Application Data

(63) Continuation of application No. 12/919,220, filed as application No. PCT/IB2009/050752 on Feb. 25, 2009, now abandoned.

(30) Foreign Application Priority Data

Mar. 3, 2008 (EP) ................................. 08152217
Jun. 5, 2008 (EP) ................................. 08157678

(51) Int. Cl.
*A61B 5/00* (2006.01)
*A61B 8/08* (2006.01)
(Continued)

(52) U.S. Cl.
CPC .......... *A61B 5/6852* (2013.01); *A61B 5/0066* (2013.01); *A61B 5/6848* (2013.01);
(Continued)

(58) Field of Classification Search
CPC ........................... A61B 5/6852; A61B 5/0066
See application file for complete search history.

(56) References Cited

U.S. PATENT DOCUMENTS 5,318,023 A 6/1994 Vari et al.
5,495,541 A 2/1996 Murray et al.
(Continued)

FOREIGN PATENT DOCUMENTS

JP H05508097 A 11/1993
JP 2001524339 A 12/2001
(Continued)

OTHER PUBLICATIONS

Bigio et al., "Diagnosis of Breast Cancer Using Elastic-Scattering Spectroscopy: Preliminary Clinical Results", Journal of Biomedical Optics, vol. 5, No. 2, Apr. 2000, pp. 221-228.
(Continued)

*Primary Examiner* — Joseph M Santos Rodriguez

(57) ABSTRACT

A system for providing integrated guidance for positioning a biopsy device and estimating tumor size in a body has two levels of guidance: a coarse guidance and a fine guidance. The system includes a non-invasive imaging system for obtaining an image of the biopsy device in the body, for providing the coarse guidance. Furthermore, the system includes an optical element mounted on the needle for obtaining optical information discriminating tissue in the body, for providing the fine guidance.

4 Claims, 8 Drawing Sheets

(51) Int. Cl.
*A61B 6/00* (2006.01)
*A61B 6/12* (2006.01)
*A61B 17/34* (2006.01)
*A61B 10/02* (2006.01)
*A61B 90/00* (2016.01)

(52) U.S. Cl.
CPC .............. *A61B 6/12* (2013.01); *A61B 6/5247* (2013.01); *A61B 8/0833* (2013.01); *A61B 8/0841* (2013.01); *A61B 8/5238* (2013.01); *A61B 10/0275* (2013.01); *A61B 17/3417* (2013.01); *A61B 2090/3614* (2016.02)

(56) References Cited

U.S. PATENT DOCUMENTS

| | | |
|---|---|---|
| 5,638,819 A | 6/1997 | Manwaring et al. |
| 5,846,513 A | 12/1998 | Carroll et al. |
| 6,011,889 A | 1/2000 | Daniel et al. |
| 6,233,476 B1 | 5/2001 | Strommer et al. |
| 6,296,608 B1 | 10/2001 | Daniels et al. |
| 6,487,431 B1 | 11/2002 | Iwano et al. |
| 6,538,726 B2 | 3/2003 | Dejung et al. |
| 6,564,087 B1 | 5/2003 | Pitris et al. |
| 6,580,938 B1 | 6/2003 | Acker |
| 7,025,765 B2 | 4/2006 | Balbierz et al. |
| 7,204,826 B2 | 4/2007 | Tremaglio et al. |
| 7,769,426 B2 | 8/2010 | Hibner et al. |
| 7,945,312 B2 | 5/2011 | Hular et al. |
| 2002/0103439 A1 | 8/2002 | Zeng et al. |
| 2004/0138528 A1 | 7/2004 | Richter et al. |
| 2005/0182295 A1 | 8/2005 | Soper et al. |
| 2005/0203419 A1 | 9/2005 | Ramanujam et al. |
| 2006/0115054 A1 | 6/2006 | Yatsenko et al. |
| 2007/0191680 A1 | 8/2007 | Sato |
| 2007/0191716 A1 | 8/2007 | Goldberger et al. |
| 2007/0238997 A1 | 10/2007 | Camus |
| 2007/0270689 A1 | 11/2007 | Lothert |
| 2008/0125634 A1 | 5/2008 | Ryan et al. |
| 2009/0086905 A1 | 4/2009 | Boyden et al. |
| 2009/0919220 | 12/2010 | Hendriks et al. |
| 2010/0331782 A1 | 12/2010 | Hendriks et al. |

FOREIGN PATENT DOCUMENTS

| | | |
|---|---|---|
| JP | 2001524863 A | 12/2001 |
| JP | 2003520062 A | 7/2003 |
| JP | 2005501586 A | 1/2005 |
| JP | 2005118134 A | 5/2005 |
| JP | 2006006919 A | 1/2006 |
| JP | 2007289223 A | 11/2007 |
| JP | 2008099923 A | 5/2008 |
| JP | 2008307072 A | 12/2008 |
| WO | 03020119 A2 | 3/2003 |
| WO | 2006116163 A2 | 11/2006 |
| WO | 2008068685 A1 | 6/2008 |
| WO | 2009109879 A2 | 9/2009 |

OTHER PUBLICATIONS

Racadio et al., "Live 3D Guidance in the Interventional Radiology Suite", Interventional Radiology AJR, Dec. 2007, vol. 189, pp. W357-W364.

Quiroga et al., "Unsupervised Spike Detection and Sorting with Wavelets and Superparamagnetic Clustering", Neural Computation, vol. 16, 2004, pp. 1661-1687.

Zhong-Sheng et al., "An Analysis of Various Methods for Computing the Envelope of a Random Signal", Applied Ocean Research, vol. 17, 1995, pp. 9-19.

International Search Report—PCT/IB2009/050752 dated Jul. 29, 2009.

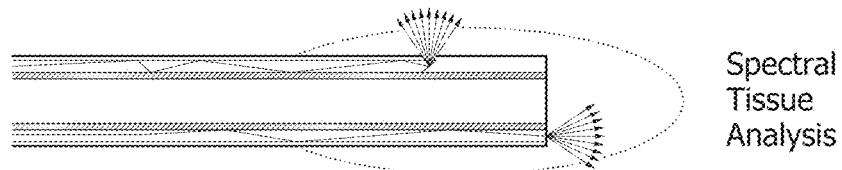
FIG. 7A  Spectral Tissue Analysis
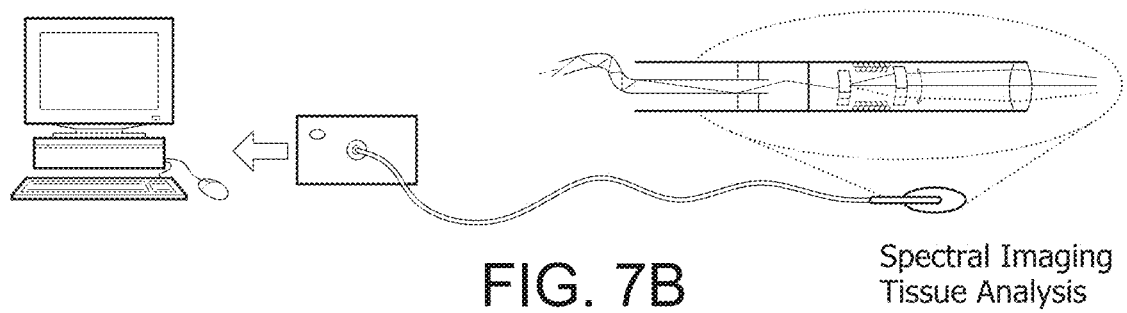
FIG. 7B  Spectral Imaging Tissue Analysis
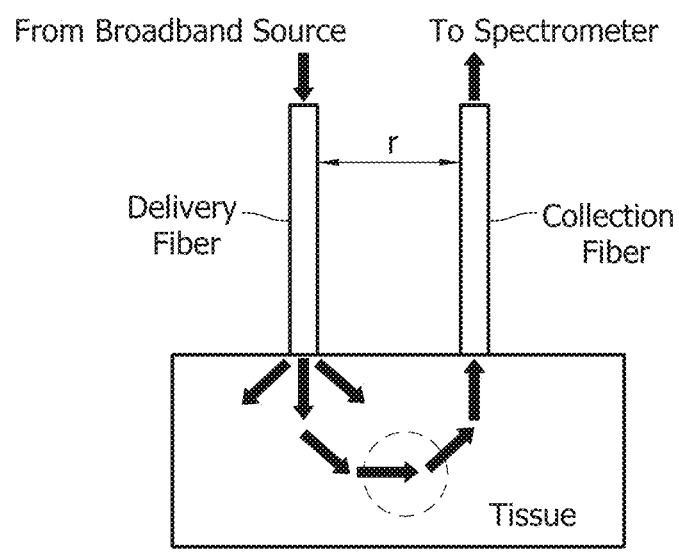
FIG. 8

BIOPSY GUIDANCE BY IMAGE-BASED X-RAY SYSTEM AND PHOTONIC NEEDLE

CROSS REFERENCE TO RELATED APPLICATION

This is a continuation of prior application Ser. No. 12/919,220 filed Aug. 25, 2015, Ser. No. 12/919,220 is a national stage filing of PCT IB2009/050752, filed Feb. 25, 2009, which claims priority from EP provisional applications 08152217.9 filed Mar. 3, 2008 and 08157678.7 filed Jun. 5, 2008.

FIELD OF THE INVENTION

The present invention relates to a system for integrated guidance for positioning a biopsy device in a body, a biopsy device and a method of positioning the same. Particularly, the invention relates to a system for and a method of providing integrated guidance for positioning the biopsy device in a body.

BACKGROUND OF THE INVENTION

For correct diagnosis of various cancer diseases biopsies are taken. This can either be done via a lumen of an endoscope or via needle biopsies. An example of a needle biopsy is shown in FIG. 1, where a biopsy is taken from the prostate via the rectum. In order to find the correct position to take the biopsy, various imaging modalities are used such as X-ray, MRI or ultrasound. In case of prostate cancer in most cases the biopsy is guided by ultrasound (see FIG. 1). Although helpful, these methods of guidance are far from optimal.

There are two major problems directly related to the biopsy:

The resolution is limited and, furthermore, these imaging modalities cannot in most cases discriminate normal and neoplastic tissue and further differentiate between benign and malignant tissue. As a result of that, there is a high level of uncertainty whether an appropriate tissue specimen is taken.

In addition to that, the biopsies are often taken blindly which leads to an additional uncertainty whether the lesion has been hit by the needle. It is clear that from the point of view of guidance improvement is required to guide the biopsy needle to the correct position in the tissue.

If the specimen taken appears to be cancerous, in most cases this cancerous tissue will be removed by surgery (especially when the tumor is well localized). Here another problem arises due to the fact that the surgeon can only use their eyes and hands (palpation) to find the tumor and have to rely on the information of pre-recorded images. These pre-recorded images provide information on the position of the tumor, but do not show the tumor boundaries. In order to help the surgeon to find the boundary a localization-wire is used. Again guiding the localization wire to the correct position is difficult.

It may be particularly difficult to find the boundaries of the tumor, in fact it is virtually impossible. As a result of that, the surgeon removes a significant amount of tissue around the core of the tumor to make sure that the entire tumor mass is removed. Although removing an additional amount of tissue around the tumor will indeed lead in most cases to complete removal, the surgeon is never sure. The number of recurrences of the cancer after removal is 30%, which indicates that some parts of the tumor remained in place and caused further tumor re-growth. One could of course increase the amount of tissue to be removed but this is in several cases difficult. In some cases vital structures are present in the tissue (nerves, important blood vessels, brain tissue). The surgeon has then to decide whether the malfunctioning due to the additional tissue outweighs the risk of not completely removing the tumor. It is important to note that when resection is not complete, the surgeon has, in fact, cut through the tumor and may cause further dissemination of the tumor. A second operation to repair these damages is very invasive and leads to sever side effects such as mutilation and loss of function of body and/or mind.

The biopsy device may also be used as a device for administering drugs or a therapy (like percutaneously using RF, microwave or cryoablation) at a certain position in the body without removing tissue, for instance for injecting a fluid at the correct location of the affected body part. The same drawbacks apply for these interventions where it is difficult to guide the biopsy device to the correct location.

SUMMARY OF THE INVENTION

It has been found that taking a biopsy in accordance with the above methods may have a number of drawbacks, such as difficulties in guiding the biopsy needle to a center of the tissue to be investigated;

difficulties in delineating the tumor boundaries (shape and size of tumor);

difficulties in taking specimen out of the body for the histological analysis without dissemination of the tumor.

It may be an object to provide for an improved guidance of a biopsy device.

This is achieved by the subject matter of the respective independent claims. Further exemplary embodiments are described in the respective dependent claims.

Generally, a system according to the invention comprises an imaging device providing images of body structures, an analyze device comprising an optical element and providing information discriminating tissue of the body, and a biopsy device. The biopsy device is adapted to be traced by the imaging device, and the optical element is integrated in the biopsy device.

In other words, the invention provides an integrated system comprising a non-invasive imaging modality (i.e., X-ray, CT, MRI, Ultrasound) that can image the inside of the body, a biopsy device including at least one optical element, the element being connected to a console capable of probing the tissue in front of or near the biopsy device with an optical modality (i.e., reflectance spectroscopy, fluorescence spectroscopy, autofluorescence spectroscopy, differential path length spectroscopy, Raman spectroscopy, optical coherence tomography, light scattering spectroscopy, multi-photon fluorescence spectroscopy), wherein the console is part of the integrated system. The non-invasive imaging modality can image the biopsy device inside the body, allowing coarse guidance of the biopsy device based on the non-invasive imaging modality. The analyze device is used to fine position the tip portion of the biopsy device in the targeted tissue. Preferably, the optical information is registered into the image of the non-invasive imaging modality. Preferably, in case the non-invasive imaging modality allows 3-dimensional imaging, the optical information is registered in the 3-dimensional coordinate frame of the image.

The biopsy device might be, on the one hand, a biopsy needle or, on the other hand, a cannula, a trocar or a catheter adapted to receive a needle by which the biopsy will be actually performed.

To have a good transmission of optical information, an optical fiber might be used. Said fiber might form a connection between the console and the biopsy device, wherein the optical fiber ends at the tip portion of the biopsy fiber and, thus, forms the optical element.

The reflectance spectra of different types of tissue are in general different due to the different molecular constitution of the tissues. As a result of measuring these spectra, we are able to identify different tissues from each other. The fact that the optical method has only a limited penetration depth, the imaging depth is only a few millimeters up to a few centimeters, guiding the needle or cannula without the guidance of the non-invasive modality is difficult because there is no overview where the needle or cannula is in space. Furthermore, without being able to register the optical information to the position of the biopsy device inside the patient means that as soon as the device is moved the previous measured data has lost its relevance.

Another aspect of the invention is that in translating the measured optical data into a tissue type can be difficult when no information about the surrounding morphology is known. Hence the decision making of the tissue characterization improves having the morphology information coming from the non-invasive imaging system as input. Hence preferably first the optical data is registered to the non-invasive imaging data, then the optical information together with the morphology information around the needle coming from the non-invasive imaging modality is used in translating the measured optical data into a tissue type in front of or near the needle. For instance when the needle is in soft tissue the optical information can be affected whether a bone structure is close by or not. Taking this into account a more reliable tissue characterization is possible.

A method of positioning a biopsy device according to the invention, comprises the steps of introducing the biopsy device into a body, visualized by means of a non-invasive imaging system, constituting a coarse guidance of the biopsy device, and fine positioning the biopsy device assisted by an analyze device comprising an optical element integrated in the biopsy device, and a console for spectroscopy obtaining optical information discriminating tissue in front of or near by the tip of the biopsy device, constituting a fine guidance of the biopsy device.

BRIEF DESCRIPTION OF THE DRAWINGS

These and other objects of the present invention are apparent from and will be elucidated with reference to the embodiments described hereinafter and will reference to the following drawings. The same or like elements are denoted by the same reference signs throughout the drawing.

FIGS. 7A and 7B show two types of fiber based needles.

FIG. 8 shows schematically an experimental setup for measuring the optical spectra.

DETAILED DESCRIPTION OF EMBODIMENTS

Figure 1:
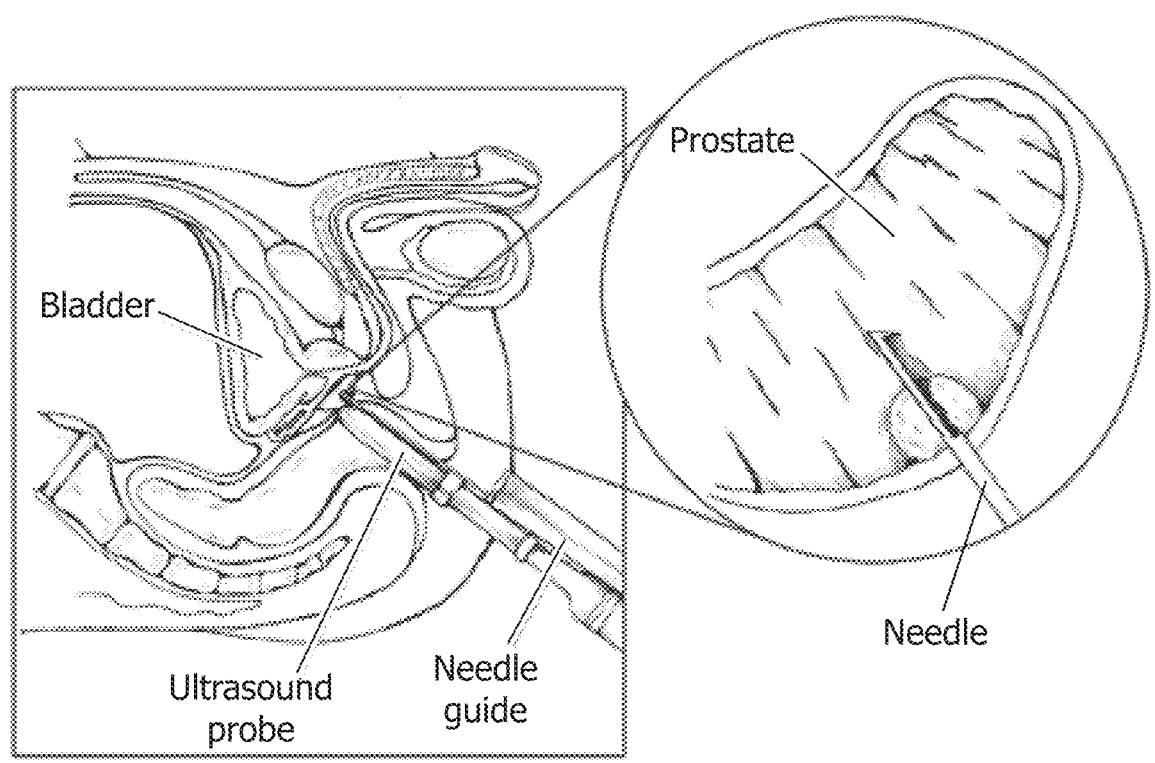
FIG. 1 shows a schematic drawing of taken a biopsy via the rectum under ultrasound guidance.
Figure 2:
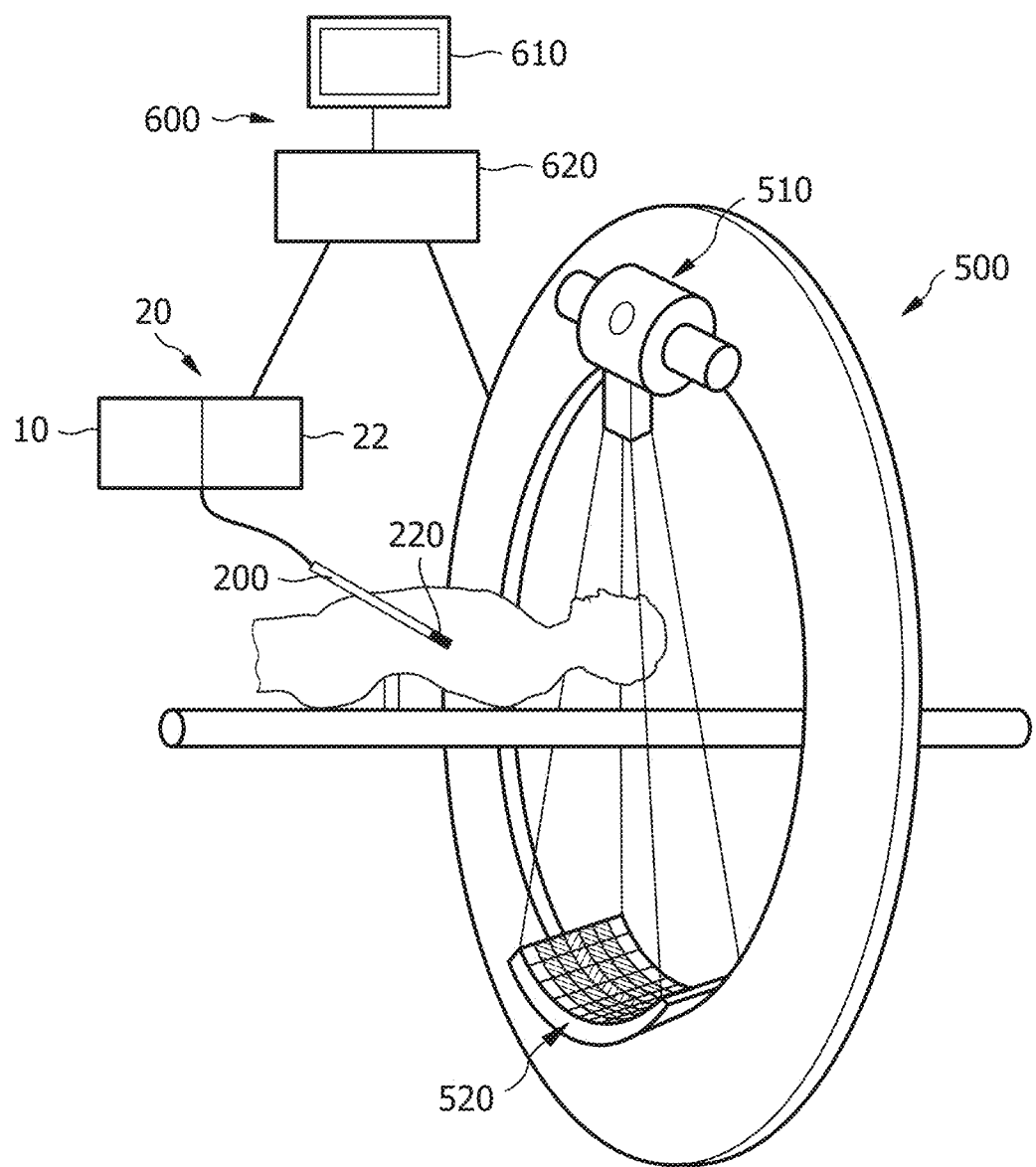
FIG. 2 shows a schematic illustration of the system for integrated guidance for positioning a biopsy device in a body, according to an exemplary embodiment of the invention.

FIG. 2 shows a system according to an exemplary embodiment of the invention. The system comprises an elongated biopsy device 200, an optical element 220 which is located at the tip portion of the biopsy device, an imaging device 500 for assisting the coarse guidance, an analyze device 20 for assisting the fine guidance, and a computing device 600. The analyze device includes a light source 10 and a spectrograph 22. The imaging device 500 includes a radiation source 510 and a detector array 520. The computing device includes a processor unit 620 for processing the signals coming from the imaging device 500 and from the analyze device 20, and a monitor 610 for monitoring information for assisting the guidance of the biopsy device in a body.

As illustrated in FIG. 2, a system for integrated guidance for positioning a biopsy device in a body, comprises an image guided X-ray based needle guidance system 500 (for instance, a system like XperGuide of Philips Medical Systems where three-dimensional isotropic soft-tissue volumes are reconstructed from rotational acquisitions and where live fluoroscopy is co-registered with the 3D data set and superimposed on it. Combining this with 3D road-mapping technique allows needle guidance as described in "Live 3d Guidance in the Interventional Radiology Suite", J. M. Racadio et al., Interventional radiology ARJ 2007; 189: W357-W364) and a biopsy needle device 200 containing an optical fiber, which is connected with an analyze device 20. The image guided needle navigation system provides integrated 2D/3D lesion imaging and an interactive image guided needle advancement monitoring, all of which is coupled to the optical information obtained by the needle, wherein the X-ray system 500 provides the coarse guidance, while the optical information received from the analyze device 20, provides the final precise guidance to the biopsy location. Preferably, the X-ray data together with the position of the needle is used as input for the optical reconstruction of which tissue is in front of the needle.

Presented below is a short summary of the characteristics of the first embodiment of the invention:

the system is able to interactively follow the biopsy needle from the incision to the target point by superimposing 2D fluro-image on 3D tissue reconstruction and provide molecular tissue information at every point along the needle trajectory that is registered to the position inside the body of the patient the region along the needle trajectory can be scanned (scan forward and scan aside) in order to provide indications on lesion existence at the molecular level preferably in reconstructing what tissue is in front of the needle the X-ray data and the position information of the needle is actively used in the optical reconstruction of what tissue is in front of the needle tumor boundaries deduced from needle scanning and from the X-ray are compared. The X-ray information gives an estimate of the shape of the tumor, but the exact boundary cannot be determined. The needle gives detailed information of the tumor boundary but this information is only obtained along the needle trajectory. By combining the X-ray shape of the tumor with the one dimensional information of the needle, a new estimate of the 3D tumor size can be calculated (see third embodiment). The newly deduced enlarged boundary will be a better estimate for the tumor boundary X-ray and needle information is further coupled to MRI images of the same area (MR data sets can be registered with the data sets produced by the X-ray machine)

biopsy needle being equipped with an optical fiber is used to position the localization wire. The localization wire containing fixation means and may be equipped with a fiber.

To demonstrate the invention a needle intervention will be described. The object from which the biopsy should be taken, is placed on, for example, a C-arm bed and the needle is mounted on a stepper motor that moves the needle in the axial direction (minimal steps of 0.25 micron). The needle is connected with optical fibers to a spectrometer. At least one of the fibers detects light reflected from the tissue, hence is an optical element.

The needle intervention consists of acquiring X-ray and fluoroscopic X-ray images while in addition optical reflectance spectra are measured by the needle containing fibers coupled to a console that is connected to the X-ray system.

After a full rotation of the C-arm around the object, it is possible to generate 3D reconstructions of the object from the X-ray information, including the position of the needle. Furthermore, advancement of the needle can be done under fluoroscopy X-ray imaging.

Figure 3A:
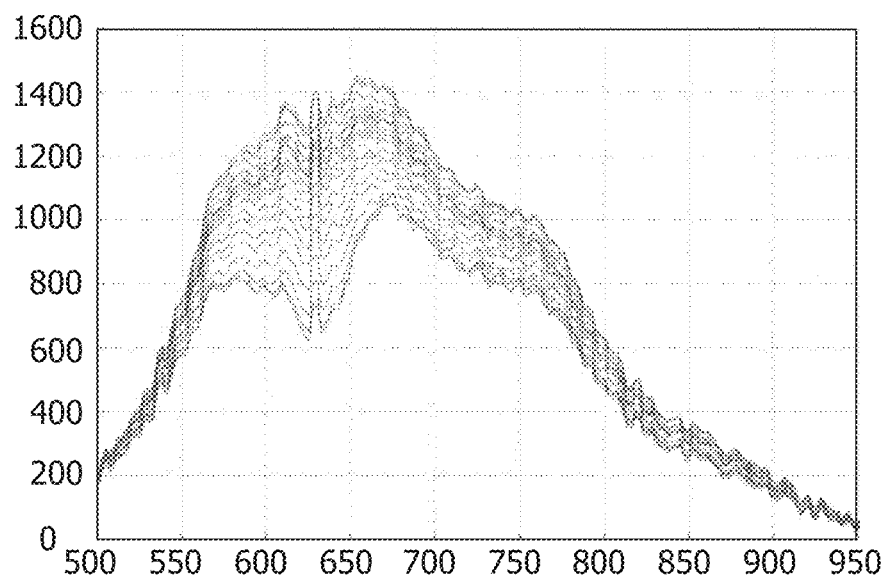
FIG. 3A shows an exemplary optical spectrum of diffuse reflectance for a plurality of locations of a tip of a biopsy device relative to an object.
Figure 3B:
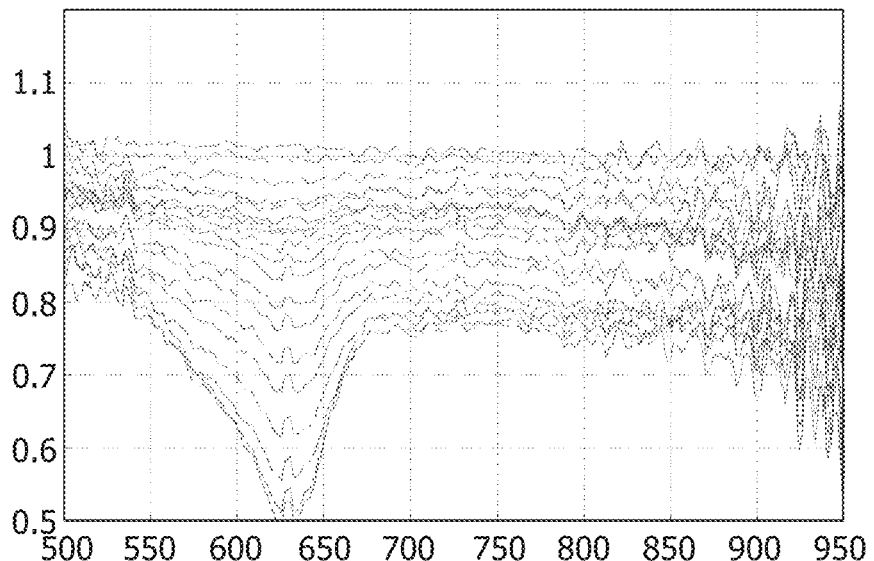
FIG. 3B shows a normalized spectrum of diffuse reflectance of FIG. 3A.

FIG. 3A show an optical spectrum which might be achieved by an analyze device for a plurality of locations of a tip of a needle relative to an object. Said object might be a tube filled with blood. The system according to the invention was utilized in a phantom. FIGS. 3A and 3B show the results, i.e., in FIG. 3A, reflectance versus wavelength for different distance between the tip of a needle and a tube located in the phantom. Wherein, the optical spectrum is measured by a needle equipped with fibers. In FIG. 3A, the vertical axis is 'Reflectance' and the horizontal axis is 'Wavelength in nm'. FIG. 3B show the normalized reflectance with respect to the signal when the needle is 32.5 mm away from the tube. Here, the vertical axis is 'normalized reflectance' and the horizontal axis is 'Wavelength in nm'.

Figure 4A:
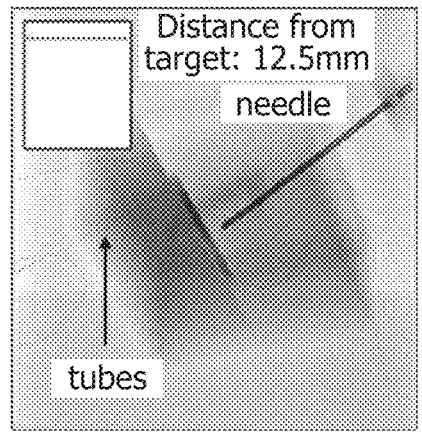
FIGS. 4A-4C show an exemplary visualization of different position of a biopsy device in a phantom, showing a fluoroscopic X-ray image of the biopsy device together with the corresponding optical reflectance spectrum (in the insert top left).
Figure 4B:
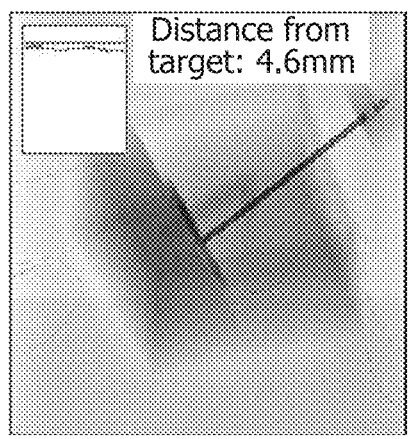
Figure 4C:
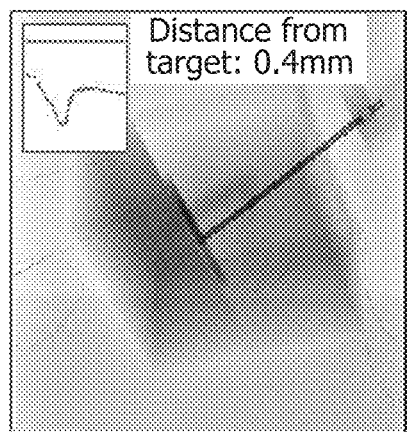

FIGS. 4A-4C show three illustrations which might be shown on a monitor to assist in guiding a biopsy device. Each illustration is mainly an image of an X-ray device, having added in the up left corner an illustration of the spectrum achieved by the analyze device. The fluoroscopy image of the X-ray device allows determining the relative position of the needle (elongated black line from the middle of each illustration to up right) with respect to the phantom (dark shadow), while the spectral information clearly shows when the small tube (black contrast line from up left to down right) is approached. It allows to fine position the needle within 100 micron accuracy. Although the information of the X-ray image and the optical information are shown in a combined image, there are various other ways to present the combined information for instance by using colors.

Figure 5:
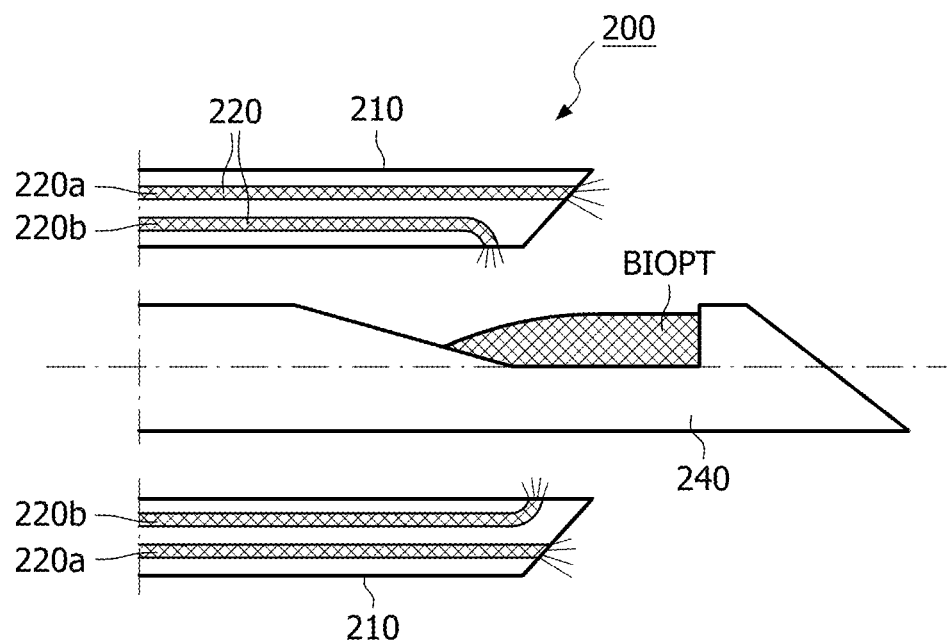
FIG. 5 shows a cross section of a biopsy device according to an exemplary embodiment of the invention, in which the optical fibers for guidance of biopsy and inspection of biopsy are located in a hollow shaft of the biopsy device.

FIG. 5 shows the tip portion of a biopsy device according to an exemplary embodiment of the invention. The biopsy device 200 comprises a shaft 210 with a fiber bundle 220. Further, the shaft 210 is adapted to accommodate a needle 240 for taking a biopt. Preferably, the fiber bundle 220 is located in the shaft 210 such that the respective ends of the fibers are located in the end surfaces of the tip portion of the biopsy device. In other words, some of the fibers might end in the front surface of the biopsy device, and/or some of the fibers might end in the vicinity of the front surface at the side surface or wall surface of the biopsy device. Furthermore, there could be some fiber ends orientated in the direction to a biopt harvested by the biopsy device, and some other fiber ends orientated in the direction to the front or the side of the biopsy device, for optical guidance prior to biopsy. In FIG. 5, fibers for optical guidance prior to biopsy are denoted with reference sign 220a, and fibers for optical inspection of the biopt are denoted with reference sign 220b.

It is noted, that any fiber might be used to emit and/or to receive light.

Figure 6:
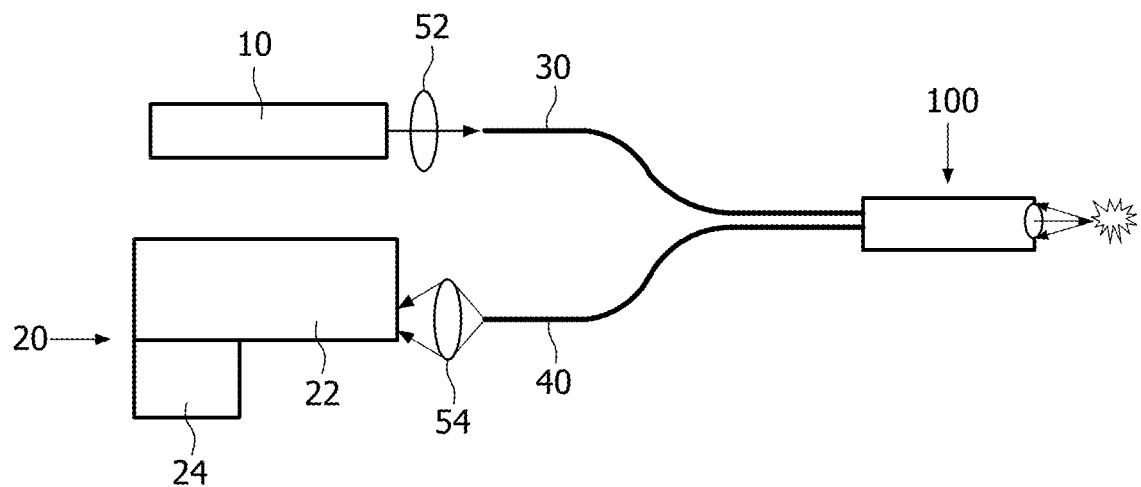
FIG. 6 shows schematically a set-up for Raman or fluorescence spectroscopy.

FIG. 6 shows further components of the system. According to this embodiment, some of the fibers 30 are coupled by way of a lens 52 to a light source 10 outside the body and are used for excitation of the tissue in front of the shaft tip of the biopsy device 100. Part of the scattered and emitted light is collected by other fibers 40 and guided to a detector, via another lens 54, which detector could be a spectrograph 22 coupled with a CCD-camera 24, where for instance an autofluorescence or Raman spectrum is recorded. Upon inspection of the spectrum it is decided to either take a biopsy with the biopsy device 100 or to move the shaft further to another position if no anomalies in the spectrum are found.

During the insertion of the biopsy device in the tissue, spectra are recorded and linked to the position of the known X-ray based needle guidance system.

For interpreting the spectra measured optically, hence translating spectra into tissue properties, the X-ray data (morphology) is used. For instance the X-ray data may provide already an indication of what type of structure could be in front of the needle, the optical data need than only to confirm or select from a few possible candidate tissues. Checking what tissue matches best with the measured spectra can then be done more reliably. Another example is if we want to be inside a certain tissue. After coarse guiding the needle with the X-ray system, the needle is fine positioned until the measured optical spectra matches with the targeted tissue.

In this way for various points, information is obtained of the tissue and is combined into the 3D image obtained by X-ray. The coarse guidance to the diseased tissue is performed by the X-ray images. The fine guidance is based on the optical information. When the final location is reached a biopsy can be taken. Optionally, the biopsy may be checked optically whether it contains the diseased tissue.

A way to provide real-time tissue characterization is by means of optical methods. For instance optical reflectance spectroscopy or Raman spectroscopy are known to provide signatures that are tissue specific. In the reflectance spectroscopy method where tissue is illuminated with a broad band light source, the reflected scattered spectral light distribution is measured. The difference in tissue properties (i.e., difference in scattering properties of the specific tissue) is visible in the changes of the spectral light distribution compared to the original spectral distribution of the illumination source. Furthermore, optical spectroscopic imaging (i.e., extending the optical imaging from a point measurement to two-dimensional imaging) provides even more detailed tissue characterization. In this case, tissue is viewed with micron resolution allowing cellular structures to become visible allowing detailed tissue analysis. When this cellular imaging is combined with optical spectroscopy, tissue characterization can be achieved, without using staining, that comes close to what currently is being used in ex-vivo pathology.

To make these methods available in a needle, the optical fiber technology is employed. By integrating fibers into the needle, optical probing at the tip of the distal end of the fiber at the tip of the needle becomes possible. The analysis can then be done at a console that is attached to the proximal end of the fiber. The console is an integral part of the integrated navigation system.

FIGS. 7A and 7B show two different types of fiber based needles. In the first type (FIG. 7A) the fibers are rigidly integrated into the needle, allowing spectroscopic analysis of the tissue near the needle tip. Since the fibers are rigidly incorporated no cellular imaging is possible. In the second type (FIG. 7B), a scanning fiber is integrated into the needle. When a lens system is mounted in front of the fiber a scanning confocal microscope is established allowing microscopic imaging of tissue. In order to scan the fiber a motor must be integrated in the needle, making the system more complex than the fixed fiber.

There are various optical techniques that can be coupled to these two ways of tissue inspection, wherein spectroscopy is one of them. An example is optical reflectance spectroscopy. The spectroscopic measurement on excised tissue is performed with the needle equipped with optical fibers as is shown in FIG. 8. The light source coupled to the fiber is a broadband light source. The reflectance spectra are measured with a spectrometer and recorded with, for example, a CCD-camera.

Figure 9:
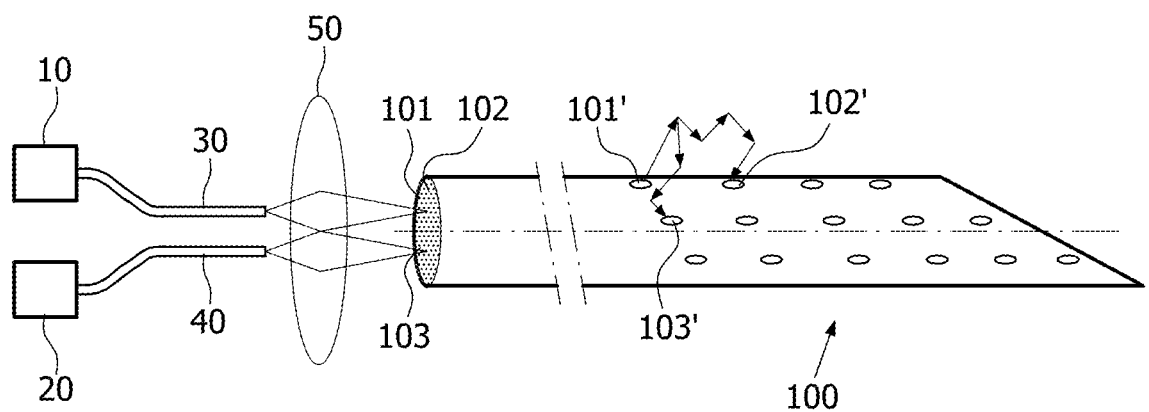
FIG. 9 shows another exemplary embodiment of a biopsy device.

FIG. 9 shows a tip portion of a biopsy device according to yet another embodiment of the invention, wherein the biopsy device 100 contains a collection of optical fibers. Although the embodiment of a biopsy device in FIG. 9 does not have a lumen, it can also be a device having a lumen. Each of the fiber entrance positions at the base of the needle (for example in FIG. 9, the positions indicated by numbers 101, 102 and 103) relates to a fiber exit position at the head of the needle (in FIG. 9 indicated by primed numbers 101', 102' and 103'). In this way the needle head is covered with various optical probe positions, wherein the ends of the respective fibers are orientated in the direction to the side of the biopsy device.

Light is coupled by way of a lens 50 from fibers 30 into the optical fibers at the base of the biopsy device, i.e. a needle, and out of other optical fibers at the base of the biopsy device into fibers 40. A light source 10, connected to an excitation fiber 30, illuminates for instance fiber 101. The light will cross the fiber and illuminate the tissue around exit position 101'. Light scattering from this position can for instance reach position 102' and 103'. The analyze device 20 is connected to fiber 40 that collects the light coming from each fiber (101, 102 and 103, respectively). The intensity of the light is a measure for the amount of absorption and scatter between exit position 101' and 102' and 103'. From these signals the tissue characteristics around the needle can be extracted. It is worth noting that this embodiment allows two-dimensional imaging of scattering and absorption properties of the tissue surrounding the needle, with a lateral resolution equal to that of the fiber-to-fiber distance. Moreover, it is also possible to perform an optical coherence scan for each fiber, which gives for each fiber a depth scan along a line. Combining these lines, a three-dimensional image of the tissue around the needle can be reconstructed, again with a lateral resolution equal to that of the fiber-to-fiber distance.

A variation of this embodiment is the implementation of fluorescence imaging and/or spectroscopic measurements. In this case source 10 and fiber 30 serve as an excitation fiber, hence to excite the fluorescent molecules and collection fiber to collect the fluorescent light emitted by the molecules.

Similar as discussed in the first embodiment a Raman spectroscopy can be performed, but now in principle for each fiber end position 101', 102', etc.

Finally, it is also possible to perform diffuse optical tomography (DOT) around the needle. This allows functional imaging in a relatively large volume around the needle similar to what is done in optical mammography. In this embodiment one or more fibers are used for (sequential) illumination of the tissue. One or more other fibers are used to collect the scattered light. Using an image reconstruction algorithm it is possible to obtain a 3D map of the optical properties in a region around the needle. The main advantage of DOT is the high penetration depth compared to other optical methods: about half of the source detector distance. The most advantageous wavelength region for DOT is the near infrared (NIR). Here the penetration depth is at its maximum and the optical properties are strongly determined by important physiologic parameters like blood content and oxygen saturation. By combining DOT at different wavelengths it is possible to translate optical parameters into physiological parameters.

The imaging methods mentioned above can rely on direct absorption and scattering properties of the tissue under investigation. However it is also possible to map fluorescence of tissue, by illuminating with the proper wavelength and simultaneously blocking the illumination wavelength at the detector side. The fluorescence can be endogenous or exogenous, i.e. with the aid of contrast agents. The specificity of the fluorescence detection can be improved by methods well known in the art such as fluorescence lifetime imaging.

Figure 10:
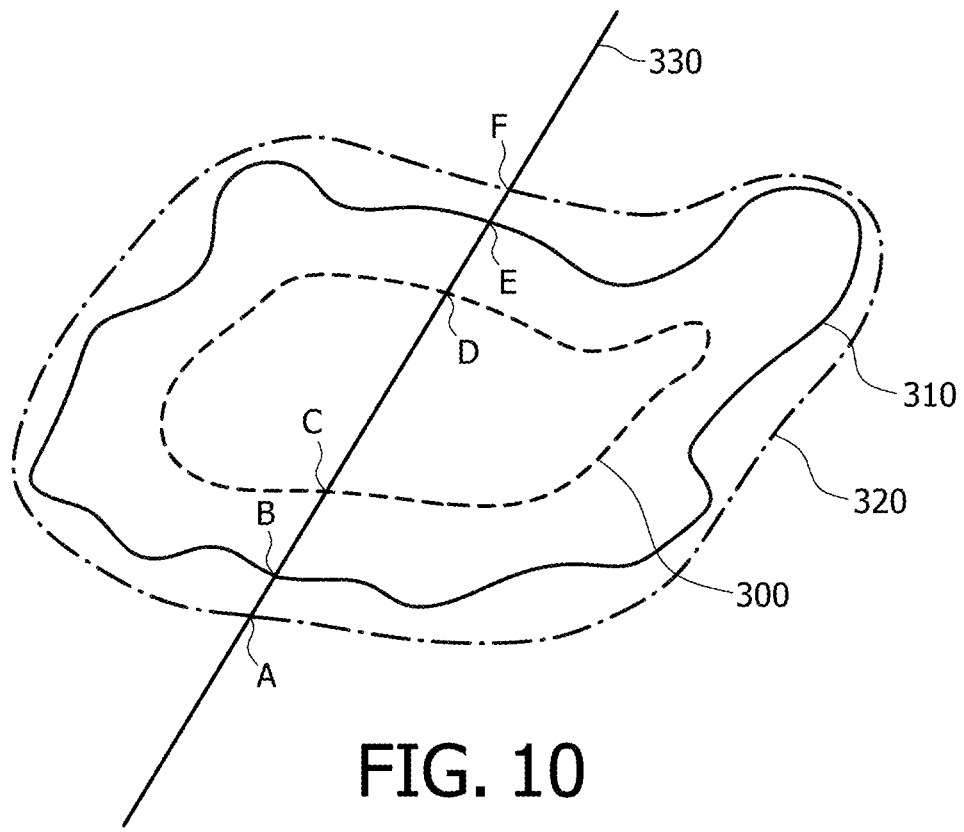
FIG. 10 shows exemplary boundaries of a tumor according to different determination methods.

According to a further aspect of the invention the tumor boundaries might be deduced from needle information and said information might be compared with information from the x-ray system. In FIG. 10, the boundary 310 deduced from the optical information (along a line 330 resulting in boundary points B and E) is in general larger than the boundary 300 of the x-ray (resulting in cross section points C and D with line 330) because of the higher sensitivity of the method. The scale factor deduced from this is used to extend the area according to that of the X-ray. The newly deduced enlarged boundary 320 will be a better estimate for the tumor boundary and can be used by the surgeon to plan an intervention.

A further embodiment is where the invention is used to guide the needle to the location of the suspicious tissue, but instead of taking a biopsy the hollow needle is used to position a localization wire. This localization wire is then used by the surgeon to find the location of the tumor to be resected.

In a further embodiment the biopsy device may also be used as a device for administering drugs or a therapy (like percutaneously using RF, microwave or cryoablation) at a certain position in the body without removing tissue, for instance for injecting a fluid at the correct location of the affected body part.

A further embodiment is for avoiding blood vessels.

By using a contrast enhanced (CE) CT acquisition, a 3D reconstruction of both arterial and venous vessel tree will be generated in addition to the soft tissue reconstruction of the brain parenchyma. Both the soft tissue and the arterial/venous vascularisation will be evaluated in order to find a location of suspicious tissue. Using the XperGuide navigation software, the needle trajectory will be defined as well as the needle advancement monitored. The needle trajectory will be defined in such a way that the planned path does not traverse any major vessel. Due to limited accuracy of needle advancement (human error), additional feedback on actual needle position with respect to the surrounding vessels is required. This can be done by using optical spectroscopy to measure the absorption properties of the tissue directly in front of the needle tip by adding an optical fiber to the needle.

Figure 11:
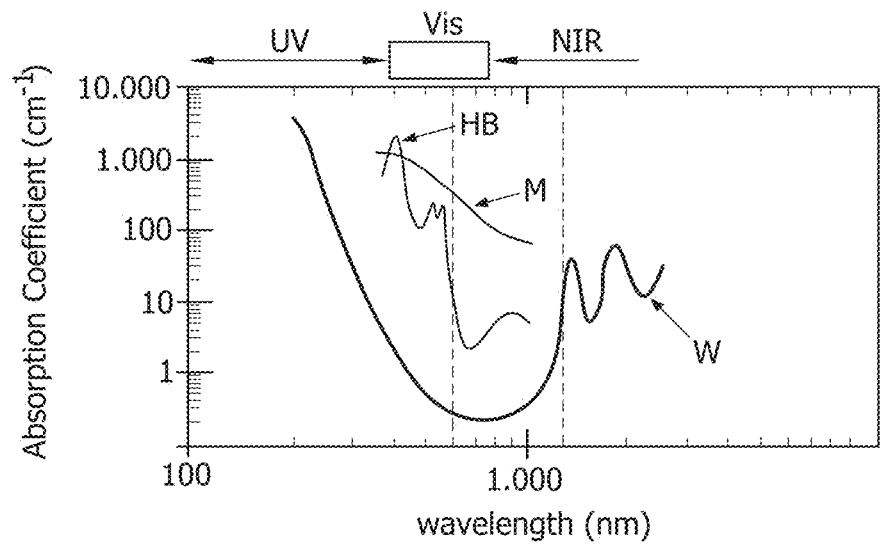
FIG. 11 shows absorption coefficients of different fluidic substances.

FIG. 11 shows absorption spectrums, wherein the vertical axis means the absorption coefficient, and the horizontal axis means the wavelength. In this exemplary diagram, the spectrum of melanosome M, of Water W and of Blood HB is depicted. The absorption spectrum of blood HB shows characteristic peaks in the visible region around 400-600 nm. From the spectrum measured in front of the biopsy needle the presence of blood can be deduced by monitoring for these peaks in the absorption spectrum. This can be done for instance by measuring the absorption at two wavelengths: one within the absorption peak (for instance at 530 nm) and one outside the peak (for instance at 633 nm). Taking the ratio of these absorption values as blood vessel monitor signal, a blood vessel will be approached when the signal significantly changes. In this way it is not necessary to measure the absorption signal absolutely, but only relatively.

Presented below is a short summary of the steps of a method according to the invention:
determination of a suspicious tissue with diagnostic scans (X-ray, CT, MRI),
3D assessment of the arterial and venous vascular tree with CE CT technique, establishment of the lesion access planning,
utilization of XperGuide to perform image guided monitoring of needle advancing, according to the planning in (3),
depiction of blood carrying vessel structures in close proximity of the needle tip with optical methods,
utilization of the optical information in order to re-adjust needle direction in order to avoid the intervening vessel structures.

Figure 12A:
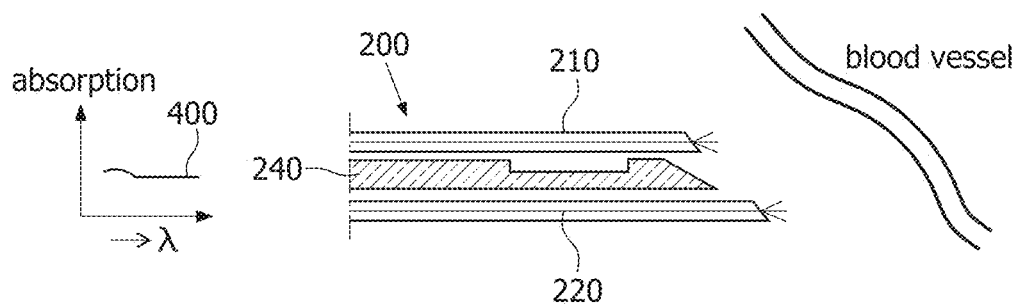
FIGS. 12A and 12B show cross sectional views illustrating the relation between the distance of a biopsy device according to an embodiment of the invention, from a blood vessel and the absorption spectrum visualized by the system according to an embodiment of the invention.
Figure 12B:
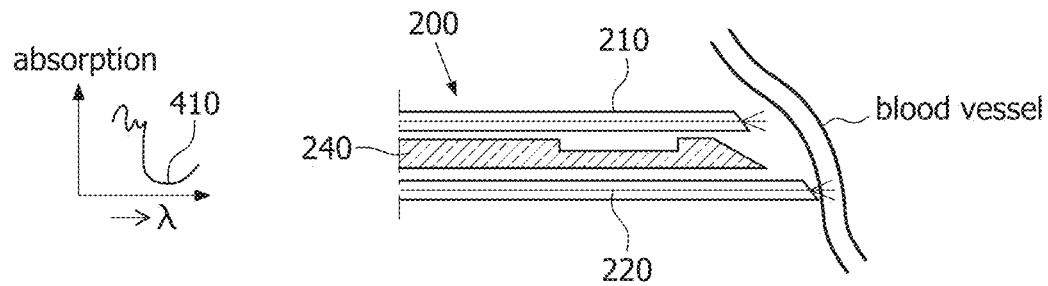

The first embodiment is focused on items (1)-(4). The shaft 210 of the biopsy device 200 contains at least one fiber 220 and is adapted to receive a needle 240 (see FIG. 12). The at least one fiber is used to illuminate the tissue in front of the fiber and also serves as collection fiber of the backscattered light. Part of the scattered and emitted light, collected by the fiber is guided to a spectrograph (see FIG. 6), where the absorption spectrum is recorded 400, 410 (see FIGS. 12A and 12B). In case a blood vessel is far away the absorption spectrum 400 does not reveal the absorptions peak characteristic for blood (see FIG. 12A). However, when a blood vessel approaches the tip or the needle the absorption spectrum 410 will show the absorption peak for blood. Once such a signal shows up, the needle advances in changed direction such that the peak is absent again.

There are various ways to measure or quantify this signal. One way is to use two lasers sources one emitting at 550 nm and the other at 633 nm. The signal relating to 550 nm probes the peak of blood, while the signal related to 633 nm is rather insensitive. Taking the ratio of these signals as triggering signal we are insensitive for surroundings deviations.

The invention and its embodiments can be applied in various clinical procedures, including:
image guided brain biopsies,
image guided brain ablations,
image guided brain neuro-stimulations,
guide the biopsy for cancer diagnosis.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 10 light source
20 analyze device
22 spectrograph
24 CCD-camera
30 excitation fiber
40 collection fiber
50, 52, 54 lens
100, 200 biopsy device
101, 102, 103 fiber entrance position
101', 102', 103' fiber exit position
210 shaft
220, 220a, 220b fiber
240 needle
300, 310, 320 boundary
330 optical information line
400, 410 absorption spectrum
500 imaging device
510 X-ray source
520 X-ray detector array
600 computing device
610 monitor
620 processor unit

The invention claimed is:

1. A system for integrated guidance for positioning a biopsy device in a body, the system being configured for deducing tumor boundaries and comprising:
an X-ray imaging device configured to provide coarse guidance, providing images of body structures, the X-ray imaging device providing X-ray information giving an estimate of a shape of a tumor,
an analyze device configured to provide fine guidance, comprising an optical element and providing one-dimensional information of a tumor boundary along a needle trajectory by discriminating tissue of the body, wherein the one-dimensional information provided by the analyze device is registered in an image provided by the X-ray imaging device, and a biopsy needle being an elongate element with a tip portion, wherein the biopsy needle is adapted to be visualized by the X-ray imaging device, and wherein the optical element is in the tip portion of the biopsy needle, wherein the system is further configured to calculate a new estimate of 3D tumor size by combining the X-ray shape of the tumor with the one_dimensional information of the analyze device.

2. The system as claimed in claim 1, wherein the optical element of the analyze device comprises an optical fiber capable of emitting and receiving of light.

3. The system as claimed in claim 2, wherein the analyze device further comprises a console for spectroscopy, wherein the console and the optical fiber are connected to each other.

4. The system as claimed in claim 3, wherein the console for spectroscopy (22) is adapted to provide information from one of the group consisting of reflectance spectroscopy, fluorescence spectroscopy, autofluorescence spectroscopy, differential path length spectroscopy, Raman spectroscopy, optical coherence tomography, light scattering spectroscopy, and multi-photon fluorescence spectroscopy.

* * * * *